United States Patent
Kim et al.

(10) Patent No.: US 8,652,058 B2
(45) Date of Patent: Feb. 18, 2014

(54) BLOOD VESSEL PRESSING CUFF, BLOOD PRESSURE MEASURING APPARATUS INCLUDING THE BLOOD VESSEL PRESSING CUFF, AND BLOOD PRESSURE MEASURING METHOD USING THE BLOOD PRESSURE MEASURING APPARATUS

(75) Inventors: Youn-ho Kim, Hwaseong-si (KR);
Kun-soo Shin, Seongnam-si (KR);
Hong-sig Kim, Seongnam-si (KR);
Byung-hoon Ko, Hwaseong-si (KR)

(73) Assignee: Samsung Electronics Co., Ltd. (KR)

(*) Notice: Subject to any disclaimer, the term of this patent is extended or adjusted under 35 U.S.C. 154(b) by 778 days.

(21) Appl. No.: 12/752,337

(22) Filed: Apr. 1, 2010

(65) Prior Publication Data

US 2011/0021932 A1    Jan. 27, 2011

(30) Foreign Application Priority Data

Jul. 21, 2009    (KR) .................. 10-2009-0066389

(51) Int. Cl.
*A61B 5/02*        (2006.01)
(52) U.S. Cl.
USPC ........................................... 600/499
(58) Field of Classification Search
USPC ........................ 600/499, 480–485
See application file for complete search history.

(56) References Cited

U.S. PATENT DOCUMENTS

| 2002/0061692 A1* | 5/2002 | Steckmann et al. ........... 442/229 |
| 2004/0181254 A1* | 9/2004 | Choi et al. .................... 606/202 |
| 2007/0260130 A1 | 11/2007 | Chin |

FOREIGN PATENT DOCUMENTS

| JP | 3141925 A | 6/1991 |
| JP | 2006-204401 A | 8/2006 |
| JP | 2006288914 A | 10/2006 |
| JP | 2008-237517 A | 10/2008 |
| KR | 1020040021641 A | 3/2004 |
| KR | 1020070041778 A | 4/2007 |
| KR | 1020090038904 A | 4/2009 |

* cited by examiner

*Primary Examiner* — Patricia Mallari
*Assistant Examiner* — Vasuda Ramachandran
(74) *Attorney, Agent, or Firm* — Cantor Colburn LLP

(57) ABSTRACT

A blood vessel pressing cuff includes a strap surrounding a body part, a first actuator disposed on the strap and including a first shape memory alloy which changes to a first shape memorized in advance, at a temperature equal to or higher than a first temperature, and a second actuator disposed on the strap and including a second shape memory alloy which changes to a second shape memorized in advance, at a temperature equal to or higher than a second temperature that is different from the first temperature. If the first shape memory alloy changes to the first shape, pressure applied to the body part surrounded by the strap is increased. Even when the first shape memory alloy changes to the first shape, if the second shape memory alloy changes to the second shape, the pressure applied to the body part surrounded by the strap is reduced.

15 Claims, 13 Drawing Sheets

BLOOD VESSEL PRESSING CUFF, BLOOD PRESSURE MEASURING APPARATUS INCLUDING THE BLOOD VESSEL PRESSING CUFF, AND BLOOD PRESSURE MEASURING METHOD USING THE BLOOD PRESSURE MEASURING APPARATUS

CROSS-REFERENCE TO RELATED APPLICATIONS

This application claims priority to Korean Patent Application No. 10-2009-0066389, filed on Jul. 21, 2009, and all the benefits accruing therefrom under 35 U.S.C. §119, the disclosure of which is incorporated herein in its entirety by reference.

BACKGROUND

1. Field

Provided is a blood vessel pressing cuff for pressing a blood vessel in order to measure blood pressure, a blood pressure measuring apparatus including the blood vessel pressing cuff, and a blood pressure measuring method using the blood pressure measuring apparatus.

2. Description of the Related Art

As people's interest in health continuously increases, various blood pressure measuring apparatuses are being developed. Blood pressure measurement methods include a Korotkoff sound method, an oscillometric method, a tonometric method, and the like. In the Korotkoff sound method, which is a typical pressure measurement method, when pressure is sufficiently applied to a body part where arterial blood flows, to stop the flow of the arterial blood and then is released, pressure at a moment when an initial pulse is heard is measured as systolic pressure and pressure at a moment when no more pulse is heard is measured as diastolic pressure.

The oscillometric method and the tonometric method are used in digital blood pressure measuring apparatuses. Like the Korotkoff sounds method, in the oscillometric method, a sphygmus wave generated when pressure is sufficiently applied to a body part where arterial blood flows to stop the flow of the arterial blood and then is released at a uniform speed, or a sphygmus wave generated when pressure is applied to the body part to raise the pressure at a uniform speed, is sensed so as to measure systolic pressure or diastolic pressure. When compared to a moment at which the sphygmus wave has a maximum amplitude, pressure when the sphygmus wave is at a certain level of the maximum amplitude may be measured as the systolic pressure or the diastolic pressure.

Alternatively, pressure when amplitudes of the sphygmus wave greatly vary may be measured as the systolic pressure or the diastolic pressure. When pressure is applied and then is released at a uniform speed, the systolic pressure is measured before the sphygmus wave reaches the maximum amplitude and the diastolic pressure is measured after the sphygmus wave has reached the maximum amplitude. On the other hand, when applied pressure is raised at a uniform speed, the systolic pressure is measured after the sphygmus wave has reached the maximum amplitude and the diastolic pressure is measured before the sphygmus wave has reached the maximum amplitude. In the tonometric method, blood pressure may be continuously measured by using the amplitude and shape of a sphygmus wave generated when pressure that does not completely stop the flow of arterial blood is applied to a body part.

SUMMARY

Provided is a blood vessel pressing cuff using shape memory alloys, which is capable of being easily formed in a small size and delicately controlling application and release of pressure, a blood pressure measuring apparatus including the blood vessel pressing cuff, and a blood pressure measuring method using the blood pressure measuring apparatus.

Additional aspects will be set forth in part in the description which follows and, in part, will be apparent from the description, or may be learned by practice of the presented embodiments.

Provided is a blood vessel pressing cuff including a strap surrounding one body part, a first actuator disposed on the strap and including a first shape memory alloy that changes to a first shape memorized in advance, at a temperature equal to or higher than a first temperature, and a second actuator disposed on the strap and including a second shape memory alloy that changes to a second shape memorized in advance, at a temperature equal to or higher than a second temperature that is different from the first temperature. If the first shape memory alloy changes to the first shape, pressure applied to the one body part surrounded by the strap is increased, and even when the first shape memory alloy changes to the first shape, if the second shape memory alloy changes to the second shape, the pressure applied to the one body part surrounded by the strap is reduced.

Provided is a blood pressure measuring apparatus including a blood vessel pressing cuff, a sensing unit sensing a sphygmus wave and a pressure of a blood vessel of a person when the blood vessel pressing cuff presses one body part of the person, and a processor calculating blood pressure of the person based on the sphygmus wave and the pressure of the blood vessel.

Provided is a blood pressure measuring method including surrounding one body part of a person with a strap of a blood pressure measuring apparatus, the blood pressure measuring apparatus including the strap, a first actuator including a first shape memory alloy, and a second actuator including a second shape memory alloy, applying pressure to the one body part surrounded by the strap, by changing a temperature of the first actuator to a temperature equal to or higher than a first temperature and thus changing the first shape memory alloy to a first shape memorized in advance, calculating blood pressure of the person based on a sphygmus wave and a pressure of a blood vessel of the person, which are sensed while the one body part is pressed, and releasing the pressure applied to the one body part surrounded by the strap, by changing a temperature of the second actuator to a temperature equal to or higher than a second temperature that is different from the first temperature and thus changing the second shape memory alloy to a second shape memorized in advance.

The first shape may be a shape of the first shape memory alloy, in which a length of the first actuator is reduced when the first shape memory alloy is changed to the first shape, and the second shape may be a shape of the second shape memory alloy, in which a length of the second actuator is increased when the second shape memory alloy is changed to the second shape.

The second shape memory alloy may return to a third shape memorized in advance, at a temperature equal to or lower than a third temperature that is between the first and second temperatures, and may have no shape memorized in advance at a temperature between the second and third temperature.

The third shape may be a shape of the second shape memory alloy, in which a length of the second actuator is reduced when the second shape memory alloy is changed to the second shape.

The first temperature may be higher than room temperature, and the second temperature may be higher than the first temperature.

The first shape may be a shape of the first shape memory alloy, in which the first actuator protrudes toward the one body part when the first shape memory alloy is changed in the first shape, and the second shape may be a shape of the second shape memory alloy, in which a length of the second actuator is increased when the second shape memory alloy is changed to the second shape.

The first shape memory alloy or the second shape memory alloy may be self-heated due to a supplied current.

The first actuator may include wires of the first shape memory alloy, which are extended in a length direction of the first actuator.

The second actuator may include wires of the second shape memory alloy, which are extended in a length direction of the second actuator.

The first actuator or the second actuator may further include heaters heating the first shape memory alloy or the second shape memory alloy.

The blood vessel pressing cuff may further include a length control unit disposed on the strap and controlling a length of the strap according to a size of the one body part surrounded by the strap.

The first actuator or the second actuator may further include an adiabatic unit including an adiabatic material that surrounds the first shape memory alloy or the second shape memory alloy, respectively.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
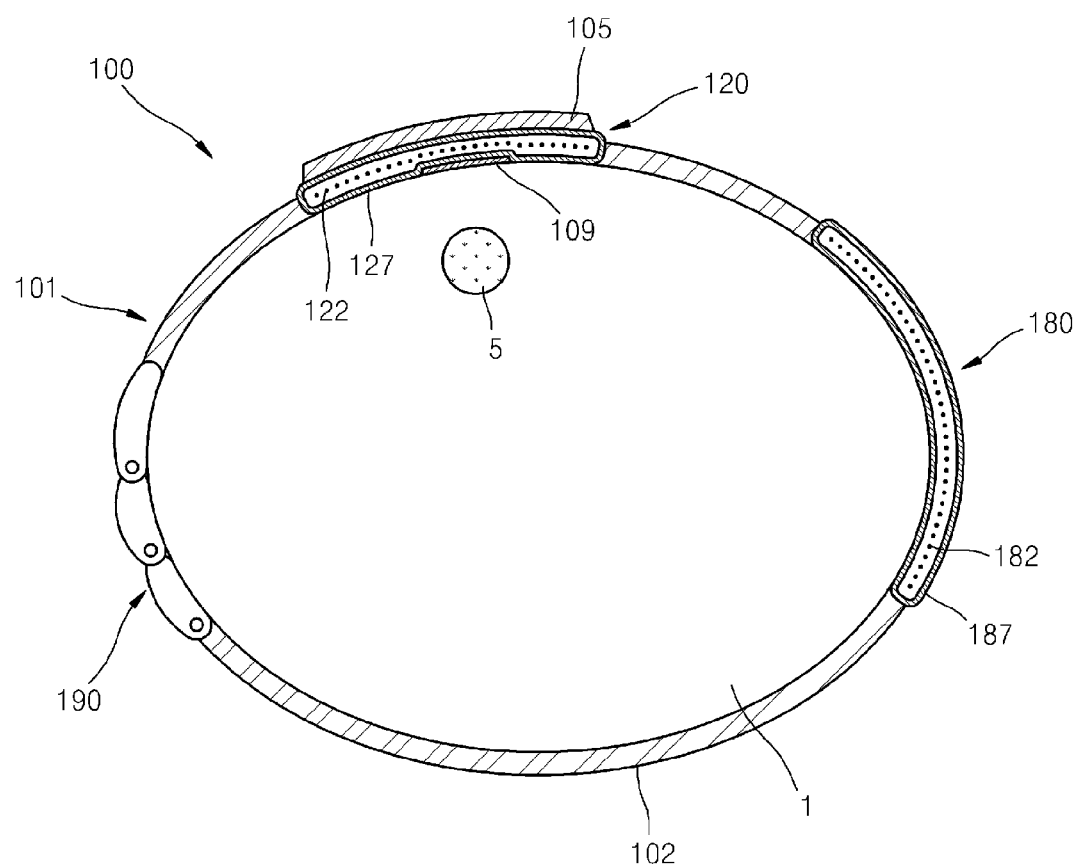
FIG. 1 is a cross-sectional view of an exemplary embodiment of a blood pressure measuring apparatus according to the present invention.

Reference will now be made in detail to embodiments, examples of which are illustrated in the accompanying drawings, wherein like reference numerals refer to like elements throughout. In this regard, the exemplary embodiments may have different forms and should not be construed as being limited to the descriptions set forth herein. Accordingly, the embodiments are merely described below, by referring to the figures, to explain aspects of the present description. In the drawings, the size and relative sizes of layers and regions may be exaggerated for clarity.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. Like numbers refer to like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the invention.

Spatially relative terms, such as "lower," "above," and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" or "above" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the invention will be described in detail with reference to the accompanying drawings.

Figure 2:
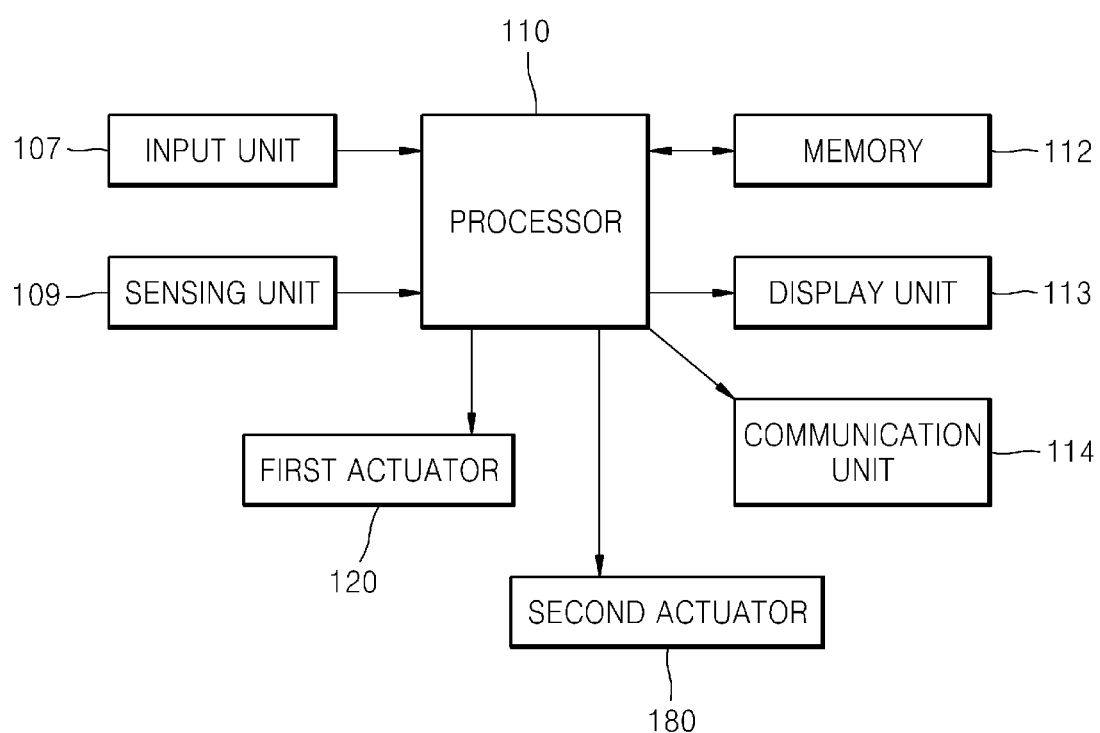
FIG. 2 is a structural block diagram of the blood pressure measuring apparatus illustrated in FIG. 1.

FIG. 1 is a cross-sectional view of an exemplary embodiment of a blood pressure measuring apparatus 100 according to the present invention. FIG. 2 is a structural block diagram of the blood pressure measuring apparatus 100 illustrated in FIG. 1.

Referring to FIGS. 1 and 2, the blood pressure measuring apparatus 100 may be worn on a wrist 1 through which a radial artery 5 passes, so as to easily sense a sphygmus wave and a pressure of a blood vessel of a person. The blood pressure measuring apparatus 100 includes a blood vessel pressing cuff 101 pressing the radial artery 5 in the wrist 1, e.g., a target part of the person, a sensing unit 109 sensing the sphygmus wave and the pressure of the radial artery 5 in the wrist 1 when the wrist 1 is pressed using the blood vessel pressing cuff 101, and a processor 110 calculating blood pressure of the person based on the sphygmus wave and the pressure of the radial artery 5, which are sensed by the sensing unit 109.

The blood pressure measuring apparatus 100 may further include a memory 112 storing data and a program which are required when the processor 110 calculates the blood pressure, an input unit 107 inputting instructions such as a blood pressure measurement instruction, a display unit 113 visually showing a blood pressure measurement result, and a communication unit 114 transmitting the blood pressure measurement result to a receiver (not shown) m such as through a wired or wireless method. The input unit 107, the processor 110, the memory 112, the display unit 113, and the communication unit 114 are included in a measurement block 105 (FIG. 1).

The blood vessel pressing cuff 101 includes a strap 102 surrounding the wrist 1, and a first actuator 120, a second actuator 180, and a length control unit 190 which are disposed on the strap 102. The first actuator 120 is disposed at a distance and separated from the second actuator 180 along a longitudinal direction of the strap 102. In FIG. 1, the first actuator 120 is disposed directly on a skin portion (e.g., an outermost surface) of the wrist 1 adjacent to the radial artery 5, and the measurement block 105 is disposed on the first actuator 120 so as to overlap with the first actuator 120. However, the measurement block 105 may not always overlap with the first actuator 120 in an alternative embodiment. Also, the sensing unit 109 may or may not overlap with the first actuator 120. The strap 102 may be a single unitary indivisible member of the blood pressure measuring apparatus 100.

The first actuator 120 includes a first shape memory alloy 122 that changes to a first shape memorized in advance, at a temperature equal to or higher than a first temperature that is higher than room temperature, and a first adiabatic unit 127 including an adiabatic material that completely surrounds the first shape memory alloy 122.

Likewise, the second actuator 180 includes a second shape memory alloy 182 and a second adiabatic unit 187 including an adiabatic material that completely surrounds the second shape memory alloy 182. The second shape memory alloy 182 changes to a second shape memorized in advance, at a temperature equal to or higher than a second temperature that is higher than the first temperature, and returns to a third shape memorized in advance, at a temperature equal to or lower than a third temperature that is between the first and second temperatures. The second shape memory alloy 182 returning to the third shape memorized in advance has no shape memorized in advance at a temperature between the second and third temperature.

A shape memory alloy, such as nitinol ("NiTi") that is an alloy of nickel (Ni) and titanium (Ti), is an alloy that memorizes a shape and changes back to the memorized shape at a shape return temperature, after being deformed from the memorized shape, such as due to an external force. The shape return temperature of the shape memory alloy may be variously set by appropriately controlling a process for memorizing the shape of the alloy. The adiabatic material of the first and second adiabatic units 127 and 187 may be, for example, meta-aramid fiber or rubber.

Figure 3:
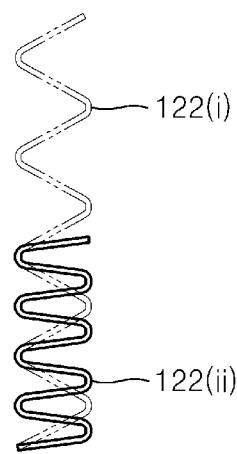
FIG. 3 is a plan view showing an exemplary embodiment of a first shape previously memorized by a first shape memory alloy illustrated in FIG. 1.

FIG. 3 is a plan view showing an exemplary embodiment of a first shape 122(ii) previously memorized by the first shape memory alloy 122 illustrated in FIG. 1. The first shape memory alloy 122 is a single unitary indivisible member.

Referring to FIG. 3, the first shape memory alloy 122 may have a substantially wire shape and may longitudinally extend in a lengthwise direction of the first actuator 120 illustrated in FIG. 1, e.g., along a circumferential direction of the wrist 1 illustrated in FIG. 1. The first shape memory alloy 122 is installed in the first actuator 120 with an initial shape 122(i) represented by a virtual (dotted) line in FIG. 3. However, the previously memorized first shape 122(ii) of the first shape memory alloy 122 is a shrunken shape compared to the initial shape 122(i). As shown in FIG. 3, the previously memorized first shape 122(ii) has a smaller length than the initial shape 122(i). Thus, if an internal temperature of the first actuator 120 is between room temperature and a first temperature, plastic deformation occurs in the first shape memory alloy 122 due to an external force. However, if heated to above the first temperature that is higher than room temperature, the first shape memory alloy 122 shrinks from the initial shape 122(i) to the first shape 122(ii), and the length of the first actuator 120 is also reduced from the initial shape 122(i) to the previously memorized first shape 122(ii).

Figure 4:
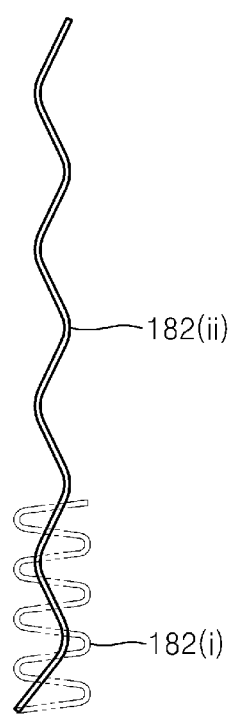
FIG. 4 is a plan view showing an exemplary embodiment of second and third shapes previously memorized by a second shape memory alloy illustrated in FIG. 1.

FIG. 4 is a plan view showing an exemplary embodiment of second and third shapes 182(ii) and 182(i) previously memorized by the second shape memory alloy 182 illustrated in FIG. 1. The second shape memory alloy 182 is a single unitary indivisible member.

Referring to FIG. 4, the second shape memory alloy 182 may also have a substantially wire shape and may longitudinally extend in a length direction of the second actuator 180 illustrated in FIG. 1, e.g., along a circumferential direction of the wrist 1 illustrated in FIG. 1. The second shape 182(ii) of the second shape memory alloy 182 is an extended shape, and the third shape 182(i) of the second shape memory alloy 182 is a shrunken shape compared to the second shape 182(ii).

The second shape memory alloy 182 is initially installed in the second actuator 180 with the third (e.g., initial) shape 182(i) represented by a virtual (dotted) line in FIG. 4. Thus, if an internal temperature of the second actuator 180 is room temperature, the second shape memory alloy 182 is maintained in the third shape 182(i) until a third temperature is reached.

If the internal temperature of the second actuator 180 exceeds the third temperature, the second shape memory alloy 182 may not be maintained in the third shape 182(i) any more, such that plastic deformation occurs in the second shape memory alloy 182 due to an external force.

If the internal temperature of the second actuator 180 is further increased from the third temperature to a second temperature, the second shape memory alloy 182 rapidly extends to the second shape 182(ii). As such, the length of the second actuator 180 is increased. The second shape memory alloy 182 returns to the third shape 182(i) memorized in advance from the second shape 182(ii), at a temperature equal to or lower than the third temperature, and has no shape memorized in advance at a temperature between the second and third temperature.

Referring back to FIGS. 1 and 2, the first and second shape memory alloys 122 and 182 are self-heated due to supplied currents, and change to previously memorized shapes if the temperatures in the first and second actuators 120 and 180 are accordingly increased. The processor 110 may control the currents supplied to the first and second actuators 120 and 180. As described above, the first and second shape memory alloys 122 and 182 are respectively surrounded by the first and second adiabatic units 127 and 187. Thus, malfunctions of the first and second shape memory alloys 122 and 182 may be prevented despite an external temperature increase caused by, for example, strong direct rays of the sun.

Figure 5:
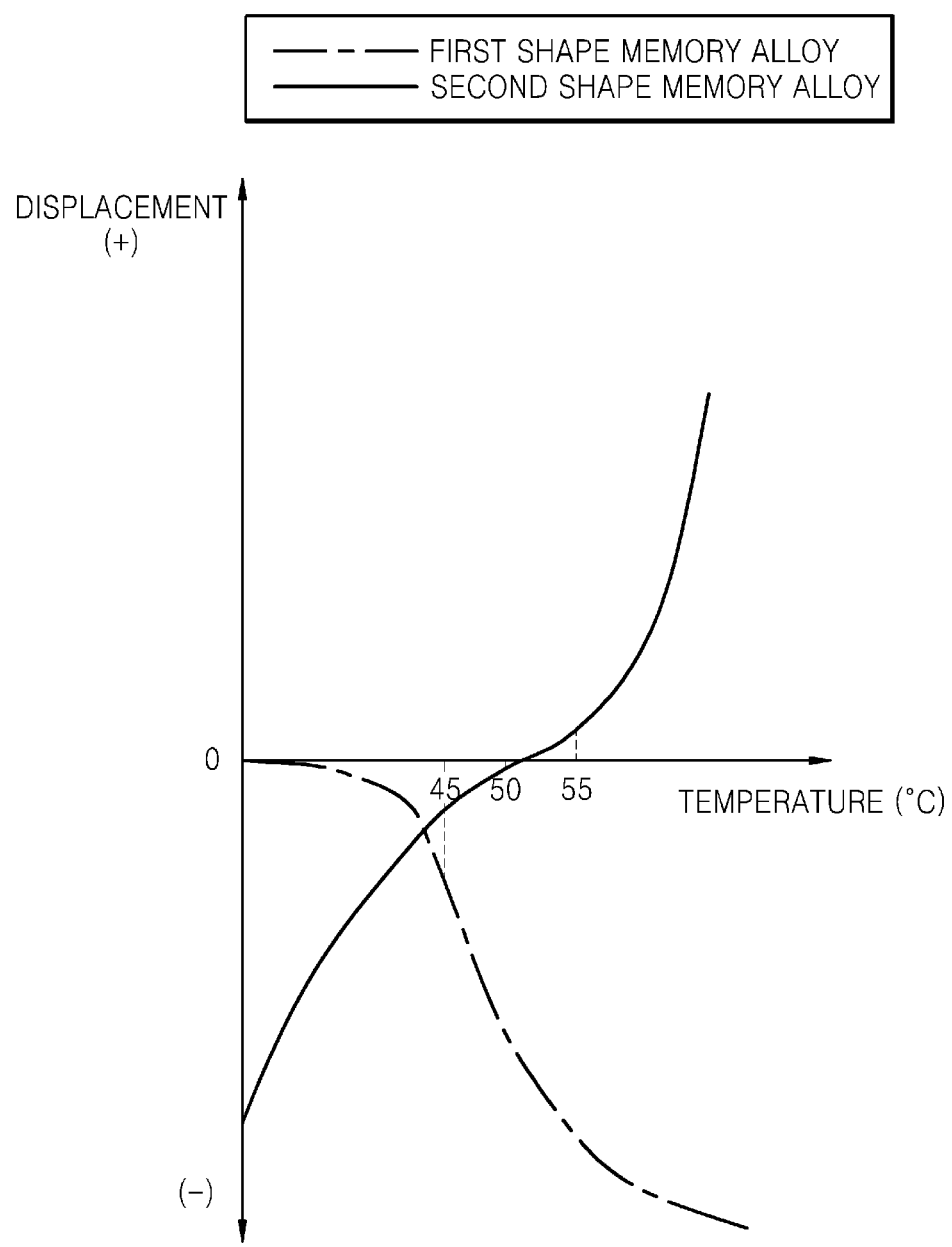
FIG. 5 is a graph showing an exemplary embodiment of correlations between temperature and displacements of the first and second shape memory alloys illustrated in FIG. 1.

FIG. 5 is a graph showing an exemplary embodiment of correlations between temperature and displacements of the first and second shape memory alloys 122 and 182 illustrated in FIG. 1. FIG. 5 will be described in conjunction with FIGS. 1, 3 and 4.

Referring to FIG. 5, for example, a first temperature at which the first shape memory alloy 122 changes from initial shape 122(i) to the first shape 122(ii) may be about 45° C., a second temperature at which the second shape memory alloy 182 changes from the third shape 182(i) to the second shape 182(ii) may be about 55° C., and a third temperature at which the second shape memory alloy 182 returns to the third shape 182(i) from the second shape 182(ii) may be about 50° C.

In order to measure blood pressure of a person, the blood pressure measuring apparatus 100 is worn around the wrist 1 of the person. In more detail, the strap 102 completely surrounds the wrist 1. The second shape memory alloy 182 is maintained in the third shape 182(i) at room temperature.

Then, the temperatures in the first and second actuators 120 and 180 are increased by applying currents to the first and second actuators 120 and 180. If an internal temperature of the first actuator 120 reaches about 45° C., e.g., the first temperature, the length of the first actuator 120 is reduced due to the first shape memory alloy 122 that changes from the initial shape 122(i) to the first shape 122(ii), and thus the wrist 1 starts to be pressed by the blood pressure measuring apparatus 100.

If an internal temperature of the second actuator 180 is increased and exceeds about 50° C., e.g., the third temperature, the second shape memory alloy 182 is not maintained in the third shape 182(i) any more, and plastic deformation occurs in the second shape memory alloy 182 due to an external force. In this case, the amount of the plastic deformation of the second shape memory alloy 182 is proportional to the strength of the external force. Since the length of the first actuator 120 is continuously reduced between about 50° C., e.g., the third temperature, and about 55° C., e.g., the second temperature, a tensile force (as the "external force") is applied to the second actuator 180 and thus the length of the second actuator 180 is increased. Accordingly, the pressure applied to the wrist 1 is smoothly increased in the temperature range from about 50° C. to about 55° C., where the length of the first actuator 120 is decreased at substantially a same time as the length of the second actuator 180 is increased. If a temperature equal to or higher than about 55° C., e.g., the second temperature, is reached, the second shape memory alloy 182 rapidly changes to the second shape 182(ii) as shown by the relatively steep slope of the line in FIG. 5, and thus the length of the second actuator 180 is rapidly increased. As such, the pressure applied to the wrist 1 is rapidly reduced.

Figure 6:
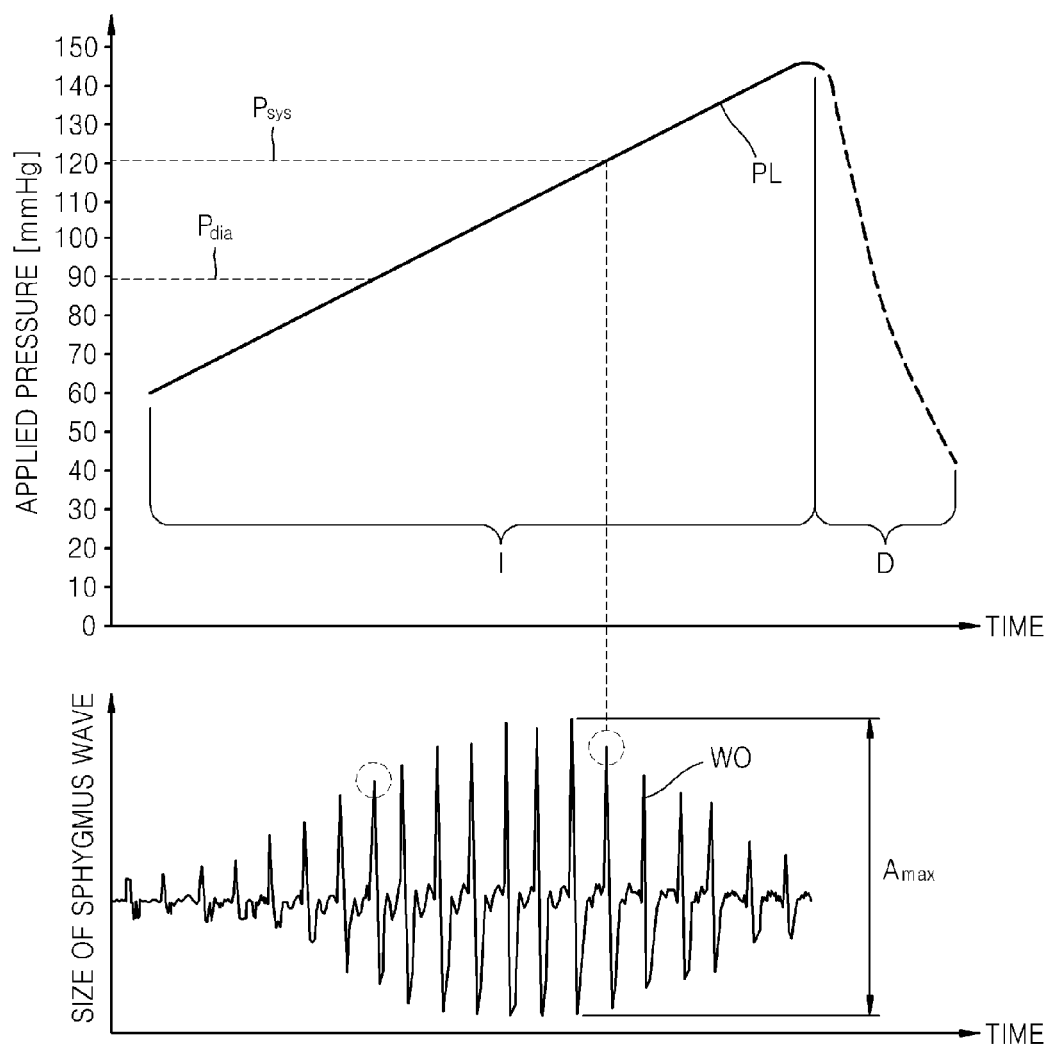
FIG. 6 illustrates graphs for describing an exemplary embodiment of a method of measuring blood pressure.

Since the pressure applied to the wrist 1 by the blood vessel pressing cuff 101 is gradually increased during a period after the temperatures in the first and second actuators 120 and 180 start to be increased and until about 55° C., e.g., the second temperature, is reached, this period is defined as a pressing period I (see FIG. 6). Since the pressure applied to the wrist 1 by the blood vessel pressing cuff 101 is rapidly reduced during a period after the temperature about equal to or higher than the second temperature is reached, this period is defined as a pressure releasing period D (see FIG. 6).

With reference to the illustrated embodiment, the blood pressure of the person is calculated based on the sphygmus wave and the pressure of the radial artery 5 of the person. After the blood pressure is calculated, if the temperatures are decreased to room temperature by blocking the currents supplied to the first and second actuators 120 and 180, the second shape memory alloy 182 shrinks and returns to the (initial) third shape 182(i). Due to a restoring force of the second shape memory alloy 182 that shrinks to the third shape 182(i), the first shape memory alloy 122 returns to the initial shape 122(i) that is the shape before shrinking to the first shape 122(ii).

An exemplary embodiment of a method of calculating blood pressure by using an oscillometric method will now be described.

FIG. 6 illustrates graphs for describing an exemplary embodiment of a method of measuring blood pressure by using an oscillometric method, and the blood pressure measuring apparatus 100 illustrated in FIG. 1.

Referring to FIG. 6, the sphygmus wave of a person during the pressing period I may be represented by, for example, a line WO. Pressure sensed by the sensing unit 109 illustrated in FIG. 1, at a time after a time when the line WO has a maximum amplitude Amax is determined as systolic pressure Psys of a person, and pressure sensed by the sensing unit 109 at a time before the time when the line WO has the maximum amplitude Amax is determined as diastolic pressure Pdia of the person. In alternative embodiments, the systolic pressure Psys and the diastolic pressure Pdia may be determined as pressures measured when the sphygmus wave has certain levels of amplitudes with reference to the maximum amplitude Amax, or may be determined as pressures measured when an envelope line of the sphygmus wave has rapidly-varying slopes.

Figure 7A:
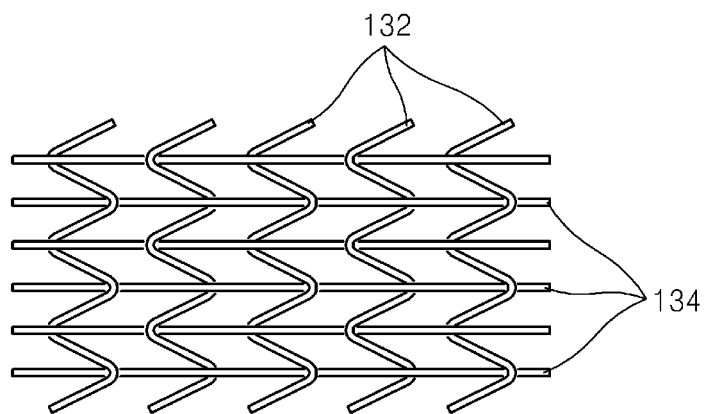
FIGS. 7A and 7B are plan views showing an exemplary embodiment of internal states of a first actuator included in the blood pressure measuring apparatus illustrated in FIG. 1.
Figure 7B:
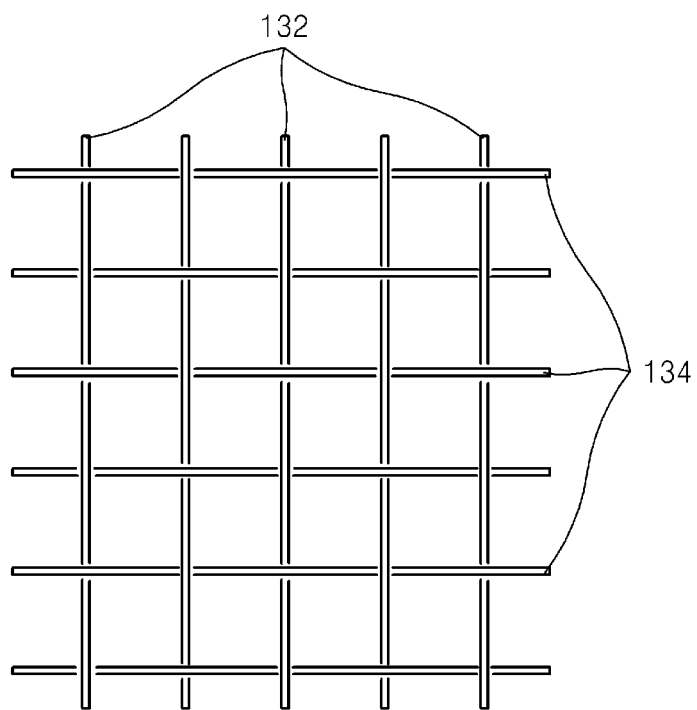

FIGS. 7A and 7B are plan views showing an exemplary embodiment of internal states of the first actuator 120 illustrated in FIG. 1. FIG. 7A illustrates a case when a first shape memory alloy 132 is shrunken, and FIG. 7B illustrates a case when the first shape memory alloy 132 is extended and includes a longer length than that of FIG. 7A.

Referring to FIGS. 7A and 7B, the first actuator 120 may have a woven structure in the plan view, in which a plurality of wires of the first shape memory alloy 132 is longitudinally extended in a single first direction, and a plurality of strands of thread 134 is longitudinally extended in a single second direction crossing the first shape memory alloy 132 wires. In addition to crossing the first shape memory alloy 132 wires, threads 134 may be disposed alternating above and below individual first shape memory alloy wires 132, respectively. A current is directly supplied to the first shape memory alloy 132 through terminals (not shown) connected to two (e.g., opposing) ends of the first shape memory alloy 132. If temperature is increased, in the woven structure, the first shape memory alloy 132 shrinks from an initial state illustrated in FIG. 7B to a state illustrated in FIG. 7A. In an embodiment, the second actuator 180 illustrated in FIG. 1 may also have the woven structure illustrated in FIGS. 7A and 7B.

Figure 8A:
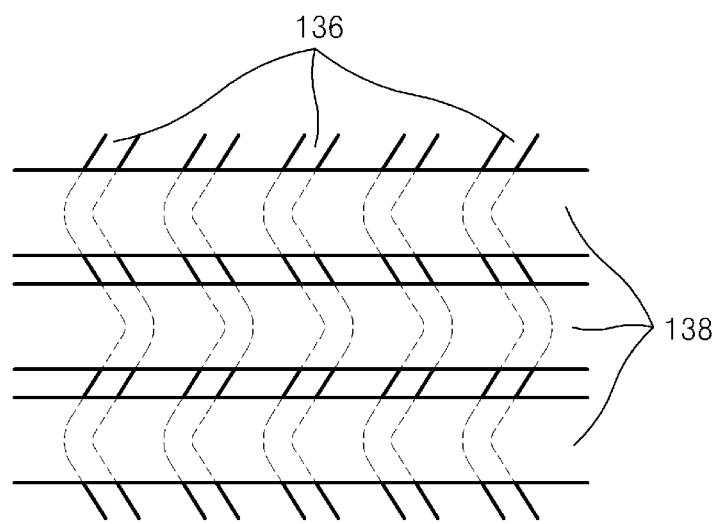
FIGS. 8A and 8B are plan views showing another exemplary embodiment of internal states of the first actuator included in the blood pressure measuring apparatus illustrated in FIG. 1.
Figure 8B:
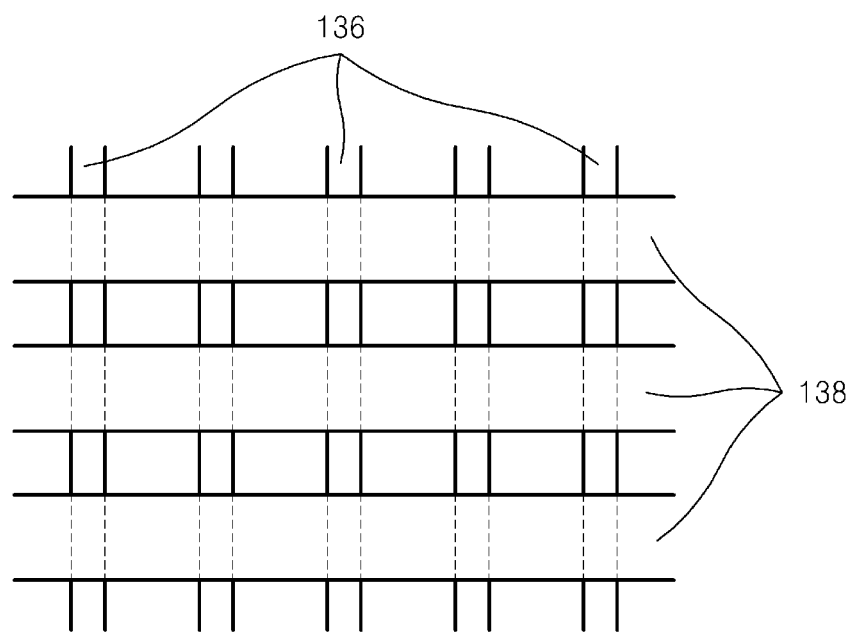

FIGS. 8A and 8B are plan views showing another exemplary embodiment of internal states of the first actuator 120 illustrated in FIG. 1. FIG. 8A illustrates a case when a first shape memory alloy 136 is shrunken, and FIG. 8B illustrates a case when the first shape memory alloy 136 is extended and includes a longer length than that of FIG. 8A.

Referring to FIGS. 8A and 8B, the first actuator 120 may have a woven structure in the plan view, in which a plurality of wires of the first shape memory alloy 136 is longitudinally extended in a single first direction, and a plurality of heaters 138 is longitudinally extended in a single second direction crossing the first shape memory alloy 136 wires. In addition to crossing the first shape memory alloy 136 wires, heaters 138 may be disposed alternating to above and below individual first shape memory alloy wires 136, respectively. A current may be supplied to the heaters 138 through terminals (not shown) connected to two (e.g., opposing) ends of the heaters 138, and thus an internal temperature of the first actuator 120 may be increased. If the internal temperature of the first actuator 120 is increased, the first shape memory alloy 136 shrinks from an initial state illustrated in FIG. 8B to a state illustrated in FIG. 8A. In an embodiment, the second actuator 180 illustrated in FIG. 1 may also have the woven structure illustrated in FIGS. 8A and 8B.

Figure 9A:
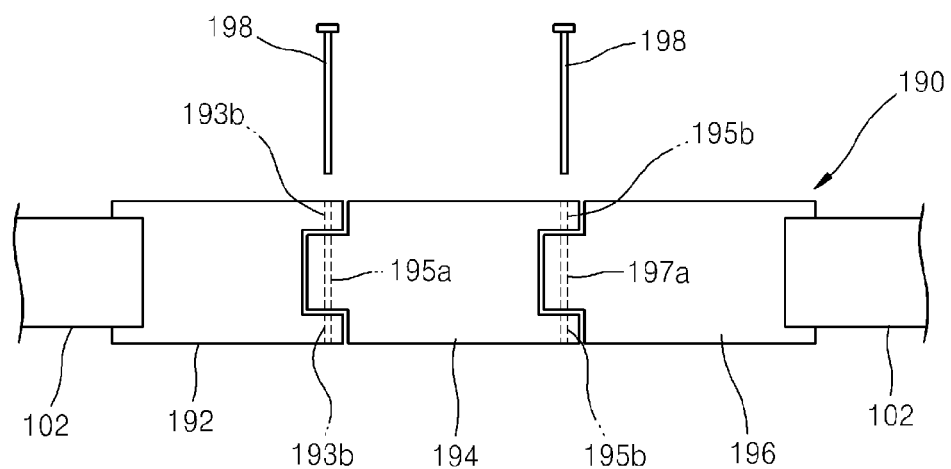
FIGS. 9A and 9B are plan views showing exemplary embodiments of a length control unit illustrated in FIG. 1.
Figure 9B:
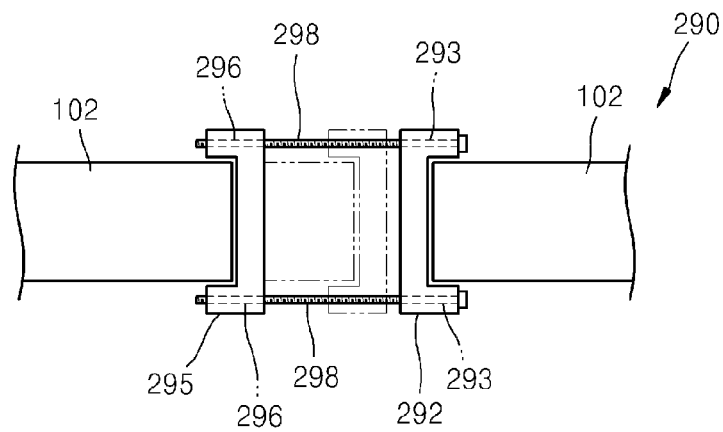

FIGS. 9A and 9B are plan views showing exemplary embodiments of the length control unit 190 illustrated in FIG. 1. The length control unit 190 is a component that controls the length of the strap 102 illustrated in FIG. 1 according to the size of the wrist 1 illustrated in FIG. 1, and more particularly, according to a circumferential length of the wrist 1.

Referring to FIG. 9A, the length control unit 190 includes a plurality of connection blocks 192, 194 and 196 that are connected to each other substantially linearly, such as in a row. Every neighboring (e.g., directly adjacent) two of the connection blocks 192, 194 and 196 includes convex and concave portions that fit together, such as by having complementing profiles. If the convex portion of each of the connection blocks 192, 194 and 196 fits into the adjacent concave portion of a neighboring one of the connection blocks 192, 194 and 196, pin holes 195a and 197a of convex portions and pin holes 193b and 195b of concave portions are correspondingly aligned, and the connection blocks 192, 194 and 196 may be connected to each other by removably inserting pins 198 into the aligned pin holes 193b and 195a, and 195b and 197a, respectively.

In one exemplary embodiment, if the wrist 1 of a person has a long circumferential length, all three of the connection blocks 192, 194 and 196 may be connected. If the wrist 1 of the person has a short circumferential length, the connection block 194 in the middle may be removed from connection with the remaining connection blocks 192 and 196, and only the connection blocks 192 and 196 may be directly connected to each other. The pins 198 combined with the pin holes 195a, 197a, 193b and 195b may solely fix the connection blocks 192, 194 and 196 to each other. An overall length of the length control unit 190 is adjustable due to the pins 198 being removably disposed in the pin holes 195a, 197a, 193b and 195b of the connection blocks 192, 194, 196, respectively. As such, the blood vessel pressing cuff 101 illustrated in FIG. 1 may be customized to a user's wrist 1, such that excessive pressing of the wrist 1 by the blood vessel pressing cuff 101 is reduced or effectively prevented.

Referring to FIG. 9B, alternatively, a length control unit 290 includes first and second brackets 292 and 295 separated from each other in a longitudinal direction of the strap 102, and connected to two (e.g. opposing) ends of the strap 102. The first and second brackets 292 and 295 are connected to each other so as to control the distance therebetween and allow the blood vessel pressing cuff 101 illustrated in FIG. 1 to be customized to a user's wrist 1.

In more detail, the first and second brackets 292 and 295 are connected to each other by screws 298 that penetrate both the first and second brackets 292 and 295. As illustrated in FIG. 9B, external threads may not be disposed on portions of the screws 298, which are kept in (e.g., overlap with) screw holes 293 disposed extending completely through the first bracket 292, and may be disposed on the other remaining portions of the screws 298 which do not overlap with the screw holes 293. The screws 298 may have a head portion disposed outside of the screw holes 293 of the first bracket 292. The head portion does not include any external threads, and may have a dimension larger than a dimension of the screw holes 293.

Also, internal threads corresponding to the external threads of the screws 298 may be disposed only in screw holes 296 disposed extending completely through the second bracket 295. In one exemplary embodiment, if the wrist 1 of the person has a long circumferential length, the screws 298 may be rotated in one direction so as to increase the distance between the first and second brackets 292 and 295. If the wrist 1 of the person has a short circumferential length, the screws 298 may be rotated in an opposite direction so as to decrease the distance between the first and second brackets 292 and 295. As such, the blood vessel pressing cuff 101 may be customized to a user's wrist 1, such that excessive pressing of the wrist 1 by the blood vessel pressing cuff 101 is reduced or effectively prevented.

Figure 10:
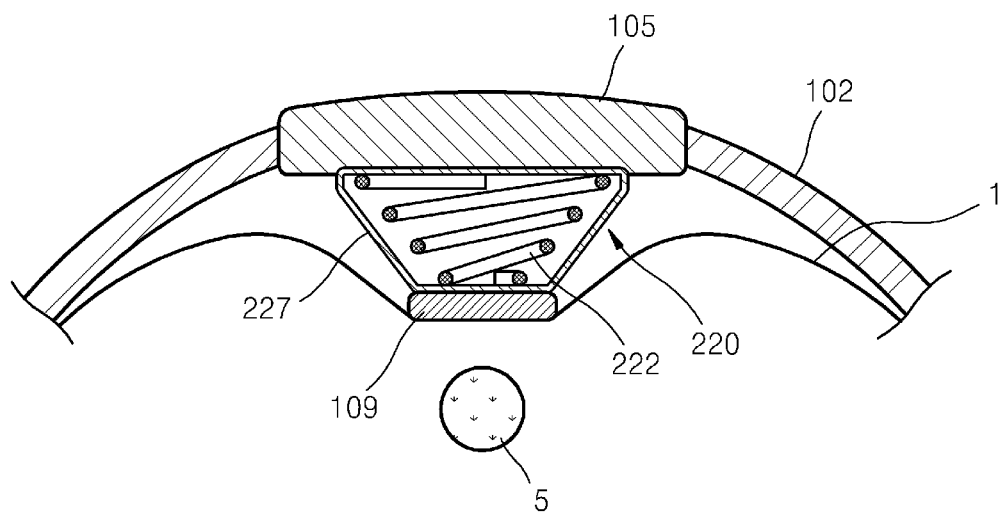
FIG. 10 is a magnified cross-sectional view of another embodiment of the first actuator included in the blood pressure measuring apparatus illustrated in FIG. 1, according to the present invention.
Figure 11A:
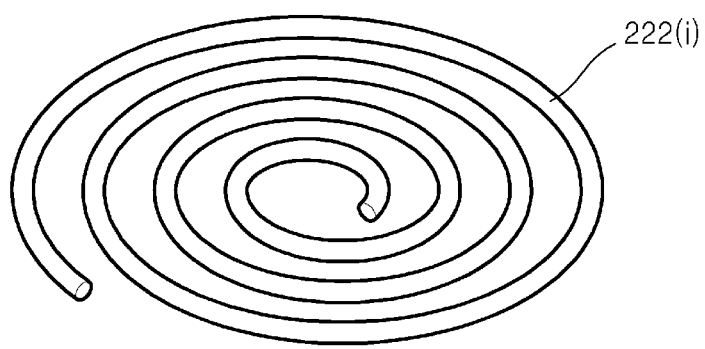
FIGS. 11A and 11B are perspective views respectively showing an initial shape and a first shape previously memorized by a first shape memory alloy illustrated in FIG. 10.
Figure 11B:
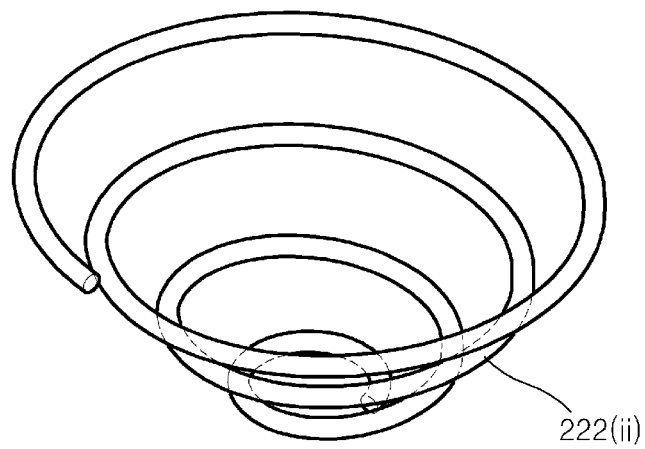

FIG. 10 is a magnified cross-sectional view of an exemplary embodiment of the first actuator included in the blood pressure measuring apparatus 100 illustrated in FIG. 1, according to the present invention. FIGS. 11A and 11B are perspective views respectively showing an initial shape 222

(*i*) and a first shape 222(*ii*) previously memorized by a first shape memory alloy 222 illustrated in FIG. 10.

Figure 12:
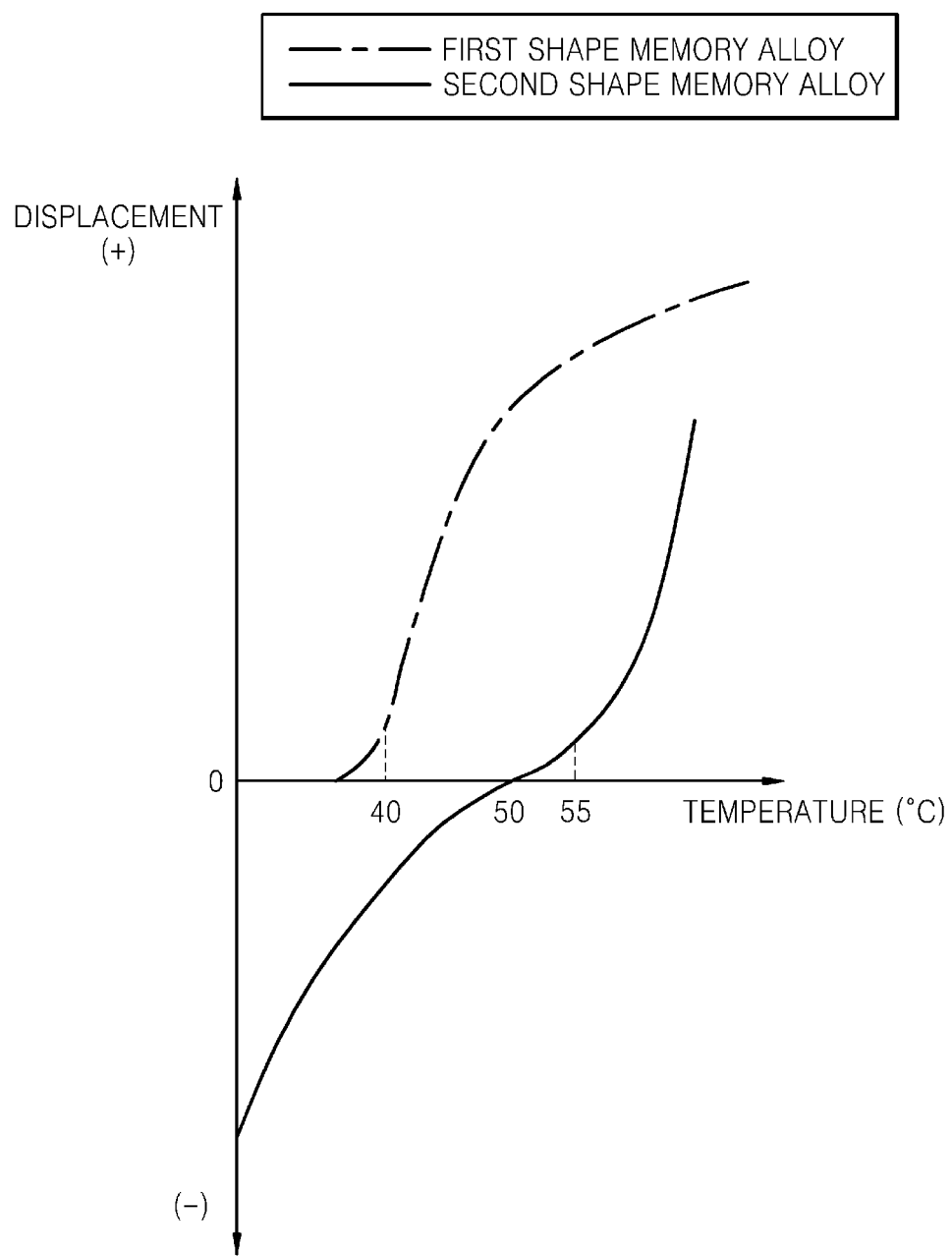
FIG. 12 is a graph showing an exemplary embodiment of correlations between temperature and displacements of the first shape memory alloy illustrated in FIG. 10 and the second shape memory alloy illustrated in FIG. 1.

FIG. 12 is a graph showing an exemplary embodiment of correlations between temperature and displacements of the first shape memory alloy 222 illustrated in FIG. 10, and the second shape memory alloy 182 illustrated in FIG. 1.

Referring to FIG. 10, a first actuator 220 according to the illustrated embodiment may be included in the blood pressure measuring apparatus 100, instead of the first actuator 120 illustrated in FIG. 1. The first actuator 220 includes the first shape memory alloy 222 that changes to the first shape 222(*ii*) at a first temperature higher than room temperature, and an adiabatic unit 227 including an adiabatic material that completely surrounds the first shape memory alloy 222. Due to the adiabatic unit 227, malfunctions of the first shape memory alloy 222 may be reduced or effectively prevented despite an external temperature increase caused by, for example, strong direct rays of the sun. A current may be directly supplied to the first shape memory alloy 222.

Referring to FIGS. 11A and 11B, the first shape memory alloy 222 is installed in the first actuator 220 with the initial shape 222(*i*). The initial shape 222(*i*) may be a spiral coil shape, where portions of the initial shape 222(*i*) are disposed substantially coplanar with each other. The spiral coil shaped first shape memory alloy 222 is a single unitary indivisible member. However, the first shape 222(*ii*) of the first shape memory alloy 222 is a shape in which one end of the spiral coil shape protrudes in one direction, e.g., portions of the first shape 222(*ii*) are not coplanar with each other. Thus, if an internal temperature of the first actuator 220 is between room temperature and the first temperature, plastic deformation occurs in the first shape memory alloy 222 due to an external force. However, if heated to above the first temperature, the first shape memory alloy 222 changes from the initial shape 222(*i*) to the first shape 222(*ii*) that protrudes in one direction. Where the first shape memory alloy is included in the first actuator 220, the first actuator 220 protrudes toward the wrist 1 illustrated in FIG. 1, since the strap 102 provides resistance to the moving of the first actuator 220 away from the wrist 1. As such, the first actuator 220 presses a skin (e.g., an outermost surface) portion of the wrist 1, which is close to the radial artery 5 illustrated in FIG. 1.

Referring to FIGS. 10, 11A, 11B and 12, the first temperature at which the first shape memory alloy 222 changes to the first shape 222(*ii*) may be, for example, about 40° C., a second temperature at which the second shape memory alloy 182 changes to the second shape 182(*ii*) illustrated in FIG. 4 may be, for example, about 55° C., and a third temperature at which the second shape memory alloy 182 returns to the third shape 182(*i*) illustrated in FIG. 4 may be, for example, about 50° C.

In an embodiment of measuring a blood pressure, in order to measure blood pressure of a person, the blood pressure measuring apparatus 100 is worn around the wrist 1 of the person. At room temperature, the second shape memory alloy 182 is maintained in the third shape 182(*i*), e.g., a shrunken shape. If currents are supplied to the first and second actuators 220 and 180, internal temperatures of the first and second actuators 220 and 180 are increased. If the internal temperature of the first actuator 220 reaches about 40° C., e.g., the first temperature, the first actuator 220 protrudes due to the first shape memory alloy 222 that changes to the first shape 222(*ii*), and thus one portion of the wrist 1, which is close to the radial artery 5, starts to be pressed.

If the internal temperature of the second actuator 180 is increased and exceeds about 50° C., e.g., the third temperature, the second shape memory alloy 182 is not maintained in the third shape 182(*i*) any more and plastic deformation occurs in the second shape memory alloy 182 due to an external force. In this case, the amount of the plastic deformation of the second shape memory alloy 182 is proportional to the strength of the external force. Since the first actuator 220 continuously protrudes toward the wrist 1 between about 50° C., e.g., the third temperature, and about 55° C., e.g., the second temperature, a tensile force is applied to the second actuator 180 and thus the length of the second actuator 180 is increased. Accordingly, the pressure applied to the wrist 1 is smoothly increased in the temperature range from about 50° C. to about 55° C.

If a temperature equal to or higher than about 55° C., e.g., the second temperature, is reached, the second shape memory alloy 182 rapidly changes to the second shape 182(*ii*) and thus the length of the second actuator 180 is rapidly increased. As such, the pressure applied to the wrist 1 is rapidly reduced. If the internal temperatures of the first and second actuators 220 and 180 are reduced to room temperature by blocking the supplied currents after the blood pressure is calculated, the first and second shape memory alloys 222 and 182 respectively return to the initial shape 222(*i*) and the third shape 182(*i*).

Figure 13:
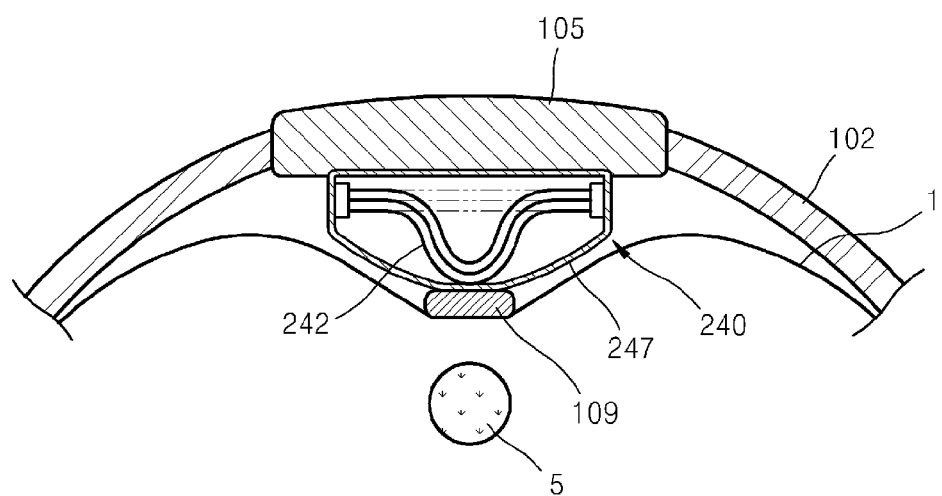
FIG. 13 is a magnified cross-sectional view of another embodiment of the first actuator included in the blood pressure measuring apparatus illustrated in FIG. 1, according to the present invention.

FIG. 13 is a magnified cross-sectional view of another exemplary embodiment of a first actuator included in the blood pressure measuring apparatus 100 illustrated in FIG. 1, according to the present invention.

Referring to FIG. 13, a first actuator 240 according to the illustrated embodiment may be included in the blood pressure measuring apparatus 100, instead of the first actuator 120 illustrated in FIG. 1 or the first actuator 220 illustrated in FIG. 10. The first actuator 240 includes a first shape memory alloy 242 that changes to a first shape memorized in advance, at a first temperature higher than room temperature, and an adiabatic unit 247 including an adiabatic material that completely surrounds the first shape memory alloy 242. Due to the adiabatic unit 247, malfunctions of the first shape memory alloy 242 may be reduced or effectively prevented despite an external temperature increase caused by, for example, strong direct rays of the sun. A current may be directly supplied to the first shape memory alloy 242.

The first shape memory alloy 242 is installed in the first actuator 240 with an initial shape represented by virtual (dotted) lines, and portions of the first shape memory alloy 242 are substantially coplanar with each other. As represented by solid lines in FIG. 13, the first shape of the first shape memory alloy 242 is a shape in which a center portion of the first shape memory alloy 242 protrudes toward the wrist 1 illustrated in FIG. 1, such that the portion of the first shape memory alloy 242 are not coplanar with each other. Thus, if the first actuator 240 is heated from room temperature to the first temperature, the first shape memory alloy 242 changes to the first shape that protrudes toward the wrist 1, and the first actuator 240 also protrudes toward the wrist 1. As such, the first actuator 240 presses a skin (e.g., an outermost surface) portion of the wrist 1, which is close to the radial artery 5 illustrated in FIG. 1.

It should be understood that the embodiments described herein should be considered in a descriptive sense only and not for purposes of limitation. Descriptions of features or aspects within each embodiment should typically be considered as available for other similar features or aspects in other embodiments.

What is claimed is:

1. A blood vessel pressing cuff comprising: a strap adapted to surround a body part; a first actuator disposed on the strap, and comprising a first shape memory alloy which changes to a first shape memorized in advance, at a temperature equal to or higher than a first temperature; and a second actuator disposed on the strap and separated from the first actuator along a length of the strap, and comprising a second shape memory alloy which changes to a second shape memorized in advance, at a temperature equal to or higher than a second temperature which is different from the first temperature, wherein the first actuator is adapted to apply an increased pressure at a target part of the body part when the first shape memory alloy changes to the first shape, and wherein the first actuator is adapted to apply a decreased pressure to the target part of the body part due to the change of the second shape memory alloy to the second shape.

2. The blood vessel pressing cuff of claim 1, wherein the first shape is a shape of the first shape memory alloy, in which a length of the first actuator is reduced when the first shape memory alloy changes to the first shape, and
wherein the second shape is a shape of the second shape memory alloy, in which a length of the second actuator is increased when the second shape memory alloy changes to the second shape.

3. The blood vessel pressing cuff of claim 1, wherein the second shape memory alloy returns to a third shape memorized in advance, at a temperature equal to or lower than a third temperature which is between the first and second temperatures, and has no shape memorized in advance at a temperature between the second and third temperature.

4. The blood vessel pressing cuff of claim 3, wherein the third shape is a shape of the second shape memory alloy, in which a length of the second actuator is reduced when the second shape memory alloy returns to the third shape.

5. The blood vessel pressing cuff of claim 1,
wherein the first temperature is higher than room temperature, and
wherein the second temperature is higher than the first temperature.

6. The blood vessel pressing cuff of claim 1,
wherein the first shape is a shape of the first shape memory alloy, in which the first actuator protrudes toward the body part when the first shape memory alloy changes to the first shape, and
wherein the second shape is a shape of the second shape memory alloy, in which a length of the second actuator is increased when the second shape memory alloy changes to the second shape.

7. The blood vessel pressing cuff of claim 1, wherein the first shape memory alloy or the second shape memory alloy is self-heated due to a supplied current.

8. The blood vessel pressing cuff of claim 1, wherein the first actuator comprises wires of the first shape memory alloy, the wires of the first shape memory alloy being longitudinally extended in a length direction of the first actuator.

9. The blood vessel pressing cuff of claim 1, wherein the second actuator comprises wires of the second shape memory alloy, the wires of the second shape memory alloy being longitudinally extended in a length direction of the second actuator.

10. The blood vessel pressing cuff of claim 1, wherein the first actuator or the second actuator further comprises heaters which heat the first shape memory alloy or the second shape memory alloy, respectively.

11. The blood vessel pressing cuff of claim 1, further comprising a length control unit disposed on the strap and controlling a length of the strap according to a size of the body part surrounded by the strap.

12. The blood vessel pressing cuff of claim 1, wherein the first actuator or the second actuator further comprises an adiabatic unit including an adiabatic material which surrounds the first shape memory alloy or the second shape memory alloy, respectively.

13. A blood pressure measuring apparatus comprising:
the blood vessel pressing cuff of claim 1;
a sensing unit sensing a sphygmus wave and a pressure of a blood vessel when the blood vessel pressing cuff presses the body part; and
a processor calculating a blood pressure based on the sphygmus wave and the pressure of the blood vessel.

14. A blood pressure measuring method comprising:
surrounding a body part with a strap of a blood pressure measuring apparatus, the blood pressure measuring apparatus comprising:
the strap,
a first actuator comprising a first shape memory alloy, and
a second actuator comprising a second shape memory alloy, the second actuator separated from the first actuator along a length of the strap;
the first actuator applying pressure to a target part of the body part, by changing a temperature of the first actuator to a temperature equal to or higher than a first temperature, which changes the first shape memory alloy to a first shape memorized in advance;
calculating blood pressure based on a sphygmus wave and a pressure of a blood vessel, which are sensed while pressure is applied to the target part of the body part; and
releasing the pressure applied by the first actuator to the target part of the body part, due to changing a temperature of the second actuator to a temperature equal to or higher than a second temperature which is different from the first temperature, which changes the second shape memory alloy to a second shape memorized in advance.

15. The method of claim 14,
wherein the first temperature is higher than room temperature, and
wherein the second temperature is higher than the first temperature.

* * * * *